US00PP31009P2

(12) United States Plant Patent
Zaiger et al.

(10) Patent No.: US PP31,009 P2
(45) Date of Patent: Nov. 5, 2019

(54) PEACH TREE NAMED 'SAUZEE SPRING'

(50) Latin Name: *Prunus persica*
Varietal Denomination: Sauzee Spring

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 16/350,293

(22) Filed: Oct. 29, 2018

(51) Int. Cl.
*A01H 5/08* (2018.01)
*A01H 6/74* (2018.01)

(52) U.S. Cl.
USPC ..... Plt./195
CPC ..... *A01H 6/7463* (2018.05)

(58) Field of Classification Search
USPC ..... Plt./195
See application file for complete search history.

*Primary Examiner* — Anne Marie Grunberg

(57) ABSTRACT

A new and distinct variety of peach tree (*Prunus persica*). The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Regular and productive bearer of medium size, peento type fruit.
3. Fruit having firm, white flesh with good flavor and eating quality.
4. Fruit having an attractive red skin color.
5. Fruit with good storage and shipping quality.

1 Drawing Sheet

Botanical designation: *Prunus persica.*
Variety denomination: 'Sauzee Spring'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

Prior Varieties

Among the existing varieties of peach and nectarine trees, which are known to us, and mentioned herein, 'Sauzee Queen' Peach (U.S. Plant Pat. No. 16,179), 'Aspen White' Peach (U.S. Plant Pat. No. 23,609) and the proprietary nectarine seedling selections '186LT97', '57Z594' and '58ZA724'.

STATEMENT REGARDING FEDERALLY SPONSORED RESEARCH AND DEVELOPMENT

Not applicable.

ORIGIN OF THE VARIETY

The new and distinct variety of peach tree (*Prunus persica*) was developed by us in our experimental orchard located near Modesto, Calif. as a first generation cross between our proprietary non-patented nectarine seedling selection '186LT97' and 'Sauzee Queen' Peach (U.S. Plant Pat. No. 16,179). The proprietary non-patented nectarine seed parent '186LT97' originated as a first generation cross between our proprietary non-patented nectarine seedling selections '57Z594' and '58ZA724'. A large number of these first generation seedlings were planted and grown on their own root system. Under close and careful observation we recognized the desirable tree and fruit characteristics of the present seedling and selected it in 2007 for additional asexual propagation and commercialization.

ASEXUAL REPRODUCTION OF THE VARIETY

In 2007 asexual reproduction of the new and distinct variety of peach tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of peach tree (*Prunus persica*) is of large size, vigorous, upright growth and a regular and productive bearer of medium size, white flesh, clingstone fruit. The fruit is further characterized by its peento shape with good storage and shipping ability. In comparison to its proprietary non-patented seed parent (186LT97) the fruit of the new variety is peento in shape compared to globose and has white flesh compared to yellow. In comparison to its pollen parent 'Sauzee Queen' Peach (U.S. Plant Pat. No. 16,179) the fruit of the new variety is approximately 6 days earlier in maturity. In comparison to the commercial variety 'Aspen White' Peach (U.S. Plant Pat. No. 23,609) the fruit of the new variety is peento in shape compared to globose and is approximately 23 days earlier in maturity.

DESCRIPTION OF THE PHOTOGRAPH

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 11 year old tree and the colors are as nearly true as is reasonably possible in a color representation of this type.

DESCRIPTION OF THE VARIETY

The following is a detailed botanical description of the new variety of peach tree, its flowers, foliage and fruit, as based on observations of 11 year old specimens grown near Modesto, Calif., with color in accordance with Munsell Book of Color published in 1958.

Tree:

*Size*.—Large, usually pruned to 3 to 3.5 meters in height and width for economical harvesting of fruit. Size varies with different cultural practices.

*Vigor*.—Vigorous, growth of 1.5 to 2 meters in height the first growing season. Varies slightly with type and fertility of soil, climatic conditions and cultural practices.

*Form*.—Upright, usually pruned to vase shape.

*Branching habit*.—Upright, crotch angle approximately 25°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 9 consecutive years. No alternate bearing observed.

*Fertility*.—Self fertile.

*Density*.—Medium dense, usually pruned to vase shape to increase air movement and sunlight to enhance fruit color and health of fruit wood.

*Hardiness*.—Hardy in all stone fruit growing areas of California. Tree grown in USDA Hardiness Zone 9. Winter chilling requirement approximately 550 hours at or below 45° F.

Trunk:

*Size*.—Medium, average circumference 45.7 cm at 25.4 cm above ground on a 11 year old tree.

*Stock*.—Medium stocky.

*Texture*.—Medium shaggy, roughness increases with age.

*Color*.—Varies from 2.5Y 4/4 to 2.5Y 3/4.

Branches:

*Size*.—Medium. Average circumference 11.4 cm at 1.2 meters above ground. Crotch angle approximately 25°, increases with heavy crop load.

*Surface texture*.—New growth relatively smooth. Mature growth medium rough, roughness increases with age.

*Lenticels*.—Average number 21 in a 25.8 square cm area. Average length 5.3 mm. Average width 2.1 mm. Color varies from 5YR 4/6 to 5YR 5/6.

*Color*.—New growth varies from 5GY 6/6 to 5GY 5/6. Mature growth varies from 5YR 4/4 to 5YR 3/4, varies with age of growth.

Leaves:

*Size*.—Large. Average length 123.9 mm. Average width 38.3 mm.

*Form*.—Lanceolate.

*Apex*.—Acuminate.

*Base*.—Cuneate.

*Margin*.—Crenate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 10.3 mm. Average width 1.3 mm. Longitudinally grooved. Surface — glabrous. Color varies from 5GY 6/6 to 5GY 5/6.

*Glands*.—Type — reniform. Size — small. Average length 1.0 mm. Average diameter 0.9 mm. Number varies from 1 to 3, average number 2. Located primarily on the base of the leaf blade and upper portion of the petiole. Color varies from 5GY 5/4 to 5GY 5/6.

*Stipules*.—Average number 2. Average length 4.3 mm. Edges — pectinate. Color varies from 5GY 6/6 to 5GY 5/6.

*Color*.—Upper surface varies from 5GY 3/4 to 7.5GY 3/4. Lower surface varies from 5GY 5/4 to 7.5GY 4/4. Midvein color varies from 10Y 7/4 to 2.5GY 6/6.

Flower buds:

*Size*.—Large. Average length 20.1 mm. Average diameter 14.0 mm.

*Hardiness*.—Hardy with respect to California winters.

*Density*.—Dense.

*Form*.—Conical, becoming elongated just before opening.

*Pedicel*.—Average length 5.0 mm. Average width 1.1 mm. Surface — pubescent. Color varies from 2.5GY 5/8 to 5GY 6/8.

*Color*.—Varies from 5RP 7/10 to 5RP 6/12.

Flowers:

*Blooming period*.—Date of First Bloom Feb. 9, 2018. Date of Petal Fall Feb. 19, 2018, varies slightly with climatic conditions.

*Size*.—Large, showy. Average height 21.7 mm. Average diameter 51.7 mm.

*Petals*.—Number — normally 5, alternately arranged to sepals. Size — large. Average length 25.6 mm. Average width 20.4 mm. Form — ovate. Petal apex — rounded. Petal base — truncate. Margin — sinuate. Arrangement — varies from overlapping to free. Both upper and lower surfaces glabrous. Color varies from 5RP 8/6 to 5RP 7/6, fades with age of flower.

*Sepals*.—Number — normally 5, alternately arranged to petals. Size — large. Average length 6.8 mm. Average width 6.3 mm. Shape — ovate, apex rounded. Margin — entire. Surface — upper surface glabrous, lower surface pubescent. Color — upper surface varies from 5GY 5/6 to 5R 2/4. Lower surface varies from 5R 2/4 to 7.5R 2/4.

*Stamens*.—Average number per flower 43. On average, the stamens are above the height of the petals. Filament color varies from N 9.5/(white) to 5RP 6/8 depending on age of flower. Anther color varies from 7.5R 4/12 to 7.5R 3/10.

*Pollen*.—Self fertile. Color varies from 2.5Y 7/12 to 2.5Y 6/10.

*Pistil*.—Number — normally one. Average length 18.9 mm. Position of stigma an average of 1.6 mm below anthers. Surface — pubescent. Color varies from 10Y 8/6 to 10Y 7/6.

*Fragrance*.—Slight aroma.

*Color*.—Varies from 5RP 7/6 to 5RP 8/4.

*Pedicel*.—Average length 6.4 mm. Average width 1.1 mm. Color varies from 2.5GY 5/8 to 5GY 5/8.

*Number flowers per flower bud*.—Normally one.

Fruit:

*Maturity when described*.—Firm ripe and ready for consumption.

*Date of first picking*.—May 15, 2018.

*Date of last picking*.—May 25, 2018, varies slightly with climatic conditions.

*Size*.—Medium. Average diameter axially 34.0 mm. Average transversely in suture plane 64.7 mm. Average weight 90.6 grams, varies slightly with fertility of the soil, amount of thinning and climatic conditions.

*Form*.—Peento shape.

*Suture*.—Slightly lipped.

*Ventral surface*.—Slightly lipped.

*Apex*.—Retuse.

*Base*.—Retuse.

*Stem cavity*.—Rounded to slightly elongated in suture plane. Average depth 4.8 mm. Average diameter 8.1 mm.

Stem:

*Size*.—Small. Average length 7.1 mm. Average diameter 3.3 mm.

*Color*.—Varies from 2.5GY 5/8 to 5GY 5/8.

Flesh:

*Ripens*.—Evenly to slightly earlier at the apex.

*Texture*.—Firm, meaty.

*Fibers*.—Few, small, tender.

*Firmness*.—Firm, comparable to other commercial peach varieties.

*Aroma*.—Moderate.

*Amydgalin*.—Undetected.

*Eating quality*.—Good.

*Flavor*.—Good, mild, sweet, sub-acid.

*Juice*.—Moderate amount, enhances flavor.

*Acidity*.—Not available.

*Brix*.—Average Brix 11.6°, varies slightly with amount of fruit per tree and climatic conditions.

*Color*.—Varies from 5Y 8.5/4 to 7.5Y 9/2, with slight bleeding around apex of 5R 4/8.

*Pit cavity*.—Average length 13.3 mm. Average width 20.3 mm. Average depth 23.0 mm. Color varies from 10Y 7/4 to 2.5GY 7/6.

Skin:

*Thickness*.—Medium.

*Surface*.—Smooth to slightly waffled.

*Pubescence*.—Moderate amount, short in length.

*Tendency to crack*.—None.

*Color*.—Ground color varies from 5Y 8.5/2 to 7.5Y 8.5/2. Overspread with 5R 4/8 to 5R 2/4.

*Tenacity*.—Tenacious to the flesh.

*Astringency*.—Slight to none.

Stone:

*Type*.—Clingstone, strong adherence to flesh.

*Size*.—Small to medium. Average length 12.3 mm. Average width 19.3 mm. Average thickness 22.0 mm.

*Form*.—Peento shape, resembles shape of fruit.

*Base*.—Flat.

*Apex*.—Nearly flat, only slightly rounded.

*Surface*.—Pitted throughout, pits vary from rounded to elongated.

*Sides*.—Unequal, one side extending further from suture plane.

*Ridges*.—Relatively smooth, narrow ridges extending from base toward apex.

*Tendency to split*.—None.

*Color*.—Varies from 10YR 7/6 to 10YR 6/8 when dry.

Kernel:

*Size*.—Small to medium. Average length 7.5 mm. Average width 10.3 mm. Average depth 8.2 mm.

*Form*.—Ovate, more round than most peach kernels.

*Viability*.—Partially viable, some embryos with incomplete development.

*Skin color*.—Varies from 2.5Y 8.5/4 to 5Y 9/4.

USE

*Dessert*.—Market — local and long distance.

Keeping quality: Good, held firm in cold storage at 38° to 42° F. for 2 weeks without internal breakdown of flesh or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program. No atypical resistances/susceptibilities have been noted under normal cultural practices.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of peach tree (*Prunus persica*), substantially as illustrated and described.

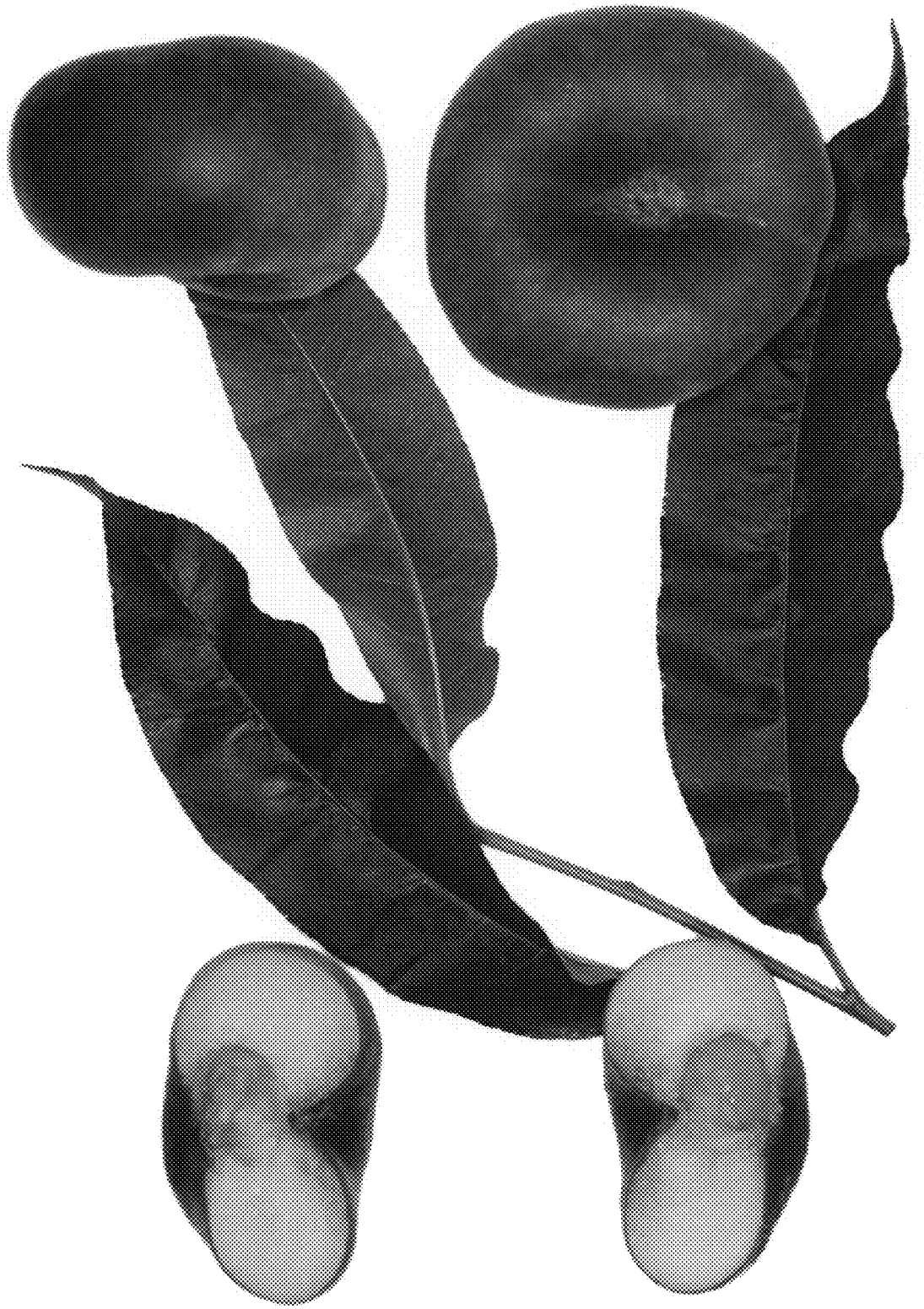

* * * * *